US010500339B2

(12) United States Patent
Gerard et al.

(10) Patent No.: US 10,500,339 B2
(45) Date of Patent: *Dec. 10, 2019

(54) IMPREGNATION PROCESS FOR A FIBROUS SUBSTRATE, A LIQUID MONOMER SYRUP FOR THE IMPREGNATION PROCESS, ITS METHOD OF POLYMERIZATION AND STRUCTURED ARTICLE OBTAINED THEREOF

(71) Applicant: Arkema France, Colombes (FR)

(72) Inventors: Pierre Gerard, Denguin (FR); Michel Glotin, Saint-Cloud (FR); Sebastien Taillemite, Chaville (FR)

(73) Assignee: Arkema France, Colombes (FR)

( * ) Notice: Subject to any disclaimer, the term of this patent is extended or adjusted under 35 U.S.C. 154(b) by 342 days.

This patent is subject to a terminal disclaimer.

(21) Appl. No.: 15/113,206

(22) PCT Filed: Jan. 22, 2015

(86) PCT No.: PCT/EP2015/051263
§ 371 (c)(1),
(2) Date: Jul. 21, 2016

(87) PCT Pub. No.: WO2015/110534
PCT Pub. Date: Jul. 30, 2015

(65) Prior Publication Data
US 2017/0009033 A1    Jan. 12, 2017

(30) Foreign Application Priority Data
Jan. 22, 2014 (FR) ..................... 14 50545

(51) Int. Cl.
*B29C 45/02* (2006.01)
*B29C 45/14* (2006.01)
*B29C 70/30* (2006.01)
*B29C 70/52* (2006.01)
*C08J 5/24* (2006.01)
*D06M 15/263* (2006.01)
*A61M 5/28* (2006.01)
*A61J 1/06* (2006.01)
*A61J 1/14* (2006.01)
*B65D 1/02* (2006.01)
*B65D 83/00* (2006.01)
*B29K 33/00* (2006.01)
*B29K 105/08* (2006.01)

(52) U.S. Cl.
CPC .............. *A61M 5/282* (2013.01); *A61J 1/067* (2013.01); *A61J 1/1468* (2015.05); *B29C 45/02* (2013.01); *B29C 45/14* (2013.01); *B29C 70/305* (2013.01); *B29C 70/52* (2013.01); *B65D 1/0215* (2013.01); *B65D 1/0292* (2013.01); *B65D 83/0094* (2013.01); *C08J 5/24* (2013.01); *D06M 15/263* (2013.01); *A61J 1/1475* (2013.01); *B29K 2033/12* (2013.01);
*B29K 2105/08* (2013.01); *C08J 2333/10* (2013.01); *C08J 2333/12* (2013.01)

(58) Field of Classification Search
CPC ........ A61J 1/067; A61J 1/1468; A61J 1/1475; A61M 5/282; C09D 4/06; C08J 5/24; C08J 2333/10; C08J 2333/06; C08J 2333/12; C08J 2425/08; C08J 2435/06; D06M 15/263; B29C 45/02; B29C 70/52; B29C 70/48; B65D 1/0215; B65D 1/0292; B65D 83/0094; C08F 265/06; B29K 2033/12; B29K 2105/08; B29K 2995/0026; B29K 2309/08; B29K 2105/0809; B29K 2033/08
See application file for complete search history.

(56) References Cited

U.S. PATENT DOCUMENTS 2,961,364 A * 11/1960 Smith .................... B29C 70/12
156/334
3,287,155 A    11/1966 Munn
5,200,107 A     4/1993 Piermattie et al.
5,530,041 A *  6/1996 Minghetti et al.
6,191,229 B1   2/2001 Sasabe et al.
(Continued)

FOREIGN PATENT DOCUMENTS

JP            9085841 A      3/1997
WO   WO-2013056845 A2 *   4/2013

Primary Examiner — Irina S Zemel
Assistant Examiner — Jeffrey S Lenihan
(74) Attorney, Agent, or Firm — Thomas F. Roland

(57) ABSTRACT

The present invention relates to an impregnation process for a fibrous substrate, a liquid composition for implementing this process and the obtained impregnated fibrous substrate. The impregnated fibrous substrate is suitable for manufacturing mechanical or structured parts or articles. In particular the present invention deals with an industrial process for impregnating a fibrous substrate or long fibers with a viscous liquid composition containing mainly methacrylic, vinylic or acrylic components either in form of monomers or polymers. This viscous composition is called hereafter liquid monomer syrup. The invention concerns also a fibrous substrate pre-impregnated with said syrup which is useful for manufacturing mechanical or structured parts or articles. More particular the impregnation of fibrous substrate with the monomer syrup is achieved in a mould. The present invention concerns also manufacturing process for manufacturing mechanical or structured parts or articles and three-dimensional mechanical or structured parts obtained by this process.

21 Claims, No Drawings

(56) References Cited

U.S. PATENT DOCUMENTS

| | | |
|---|---|---|
| 2009/0047437 A1 | 2/2009 | Yoshii et al. |
| 2010/0028710 A1 | 2/2010 | Gros et al. |
| 2014/0256850 A1 | 9/2014 | Gerard et al. |
| 2015/0218362 A1* | 8/2015 | Gerard .................. C08F 265/06 524/257 |
| 2015/0352818 A1* | 12/2015 | Glotin ..................... B32B 27/12 |
| 2016/0009878 A1* | 1/2016 | Gerard ................ D06M 13/203 523/219 |
| 2016/0017106 A1 | 1/2016 | Gerard |
| 2016/0032080 A1* | 2/2016 | Gerard ................ C08K 5/5313 524/133 |
| 2016/0090434 A1* | 3/2016 | Gerard ................ C08F 220/14 524/533 |

\* cited by examiner

IMPREGNATION PROCESS FOR A FIBROUS SUBSTRATE, A LIQUID MONOMER SYRUP FOR THE IMPREGNATION PROCESS, ITS METHOD OF POLYMERIZATION AND STRUCTURED ARTICLE OBTAINED THEREOF

This application claims benefit, under U.S.C. § 119 or § 365 of PCT Application Number PCT/EP2015/051263, filed Jan. 22, 2015, and French Patent Application Number FR14.50545, filed Jan. 22, 2014, these documents being incorporated herein by reference.

FIELD OF THE INVENTION

The present invention relates to an impregnation process for a fibrous substrate, a liquid composition for implementing this process and the obtained impregnated fibrous substrate. The impregnated fibrous substrate is suitable for manufacturing mechanical or structured parts or articles.

In particular the present invention deals with an industrial process for impregnating a fibrous substrate or long fibers with a viscous liquid composition containing mainly methacrylic, vinylic or acrylic components either in form of monomers or polymers. This viscous composition is called hereafter liquid monomer syrup. The invention concerns also a fibrous substrate pre-impregnated with said syrup which is useful for manufacturing mechanical or structured parts or articles.

More particular the impregnation of fibrous substrate with the monomer syrup is achieved in a mould.

The present invention concerns also manufacturing process for manufacturing mechanical or structured parts or articles and three-dimensional mechanical or structured parts obtained by this process.

TECHNICAL PROBLEM

Mechanical or structured parts or articles that have to absorb high stresses during their use are widely manufactured from composite materials. A composite material is a macroscopic combination of two ore more non miscible materials. The composite material constitutes at least of a matrix material that forms a continuous phase for the cohesion of the structure and a reinforcing material with various architectures for the mechanical properties.

The aim in using composite materials is to achieve a performance from the composite material that is not available from its separate constituents if used alone. Consequently composite materials are widely used in several industrial sectors as for example building, automotive, aerospace, transport, leisure, electronics, and sport notably due to their better mechanical performance (higher tensile strength, higher tensile modulus, higher fracture toughness) in comparison with homogenous materials and their low density.

The most important class in view of volume in commercial industrial scale, are composites with organic matrices, where the matrix material is a generally polymer. The principal matrix or continuous phase of a polymeric composite material is either a thermoplastic polymer or a thermosetting polymer.

Thermosetting polymers consist of crosslinked three dimensional structures. The crosslinking is obtained by curing reactive groups inside the so called prepolymer. Curing for example can be obtained by heating the polymer chains in order to crosslink and harden the material permanently.

In order to prepare the polymeric composite material the prepolymer is mixed with the other component such as glass beads or fibres or the other component which is wetted or impregnated and cured afterwards. Example for prepolymers or matrix material for thermoset polymers are unsatured polyesters, vinylesters, epoxy or phenolic ones.

A major disadvantage of a thermoset polymer matrix is its rigidity. The matrix cannot be easily shaped in other forms. Once the polymer has been cured the form is fixed. This makes also difficult the recycling of the thermoset composite material and manufactured mechanical or structured parts or articles comprising said thermoset composite material, which are burned in a cement plant or thrown into a waste dump.

Thermoplastic polymers consist of linear or branched polymers, which are usually not crosslinked. The thermoplastic polymers are heated in order to mix the constituents necessary for producing the composite material and to be cooled for setting. The limit in using thermoplastic polymers for the fabrication of composite materials is their high viscosity in the molten state in order to homogenously impregnating for example a fibrous substrate. The wetting or correct impregnation of the fibers by the thermoplastic polymer can only be achieved, if the thermoplastic resin is sufficiently fluid. In order to have a low viscosity or sufficient fluidity of the thermoplastic polymer the chain length or molecular mass shall be reduced. However a too low molecular weight has a negative impact on the performance of the composite material and on the mechanical or structured parts especially their mechanical properties as the deformation modulus.

Another way to reduce the viscosity in an important way of the thermoplastic polymer is to increase the temperature. Consequently the continuous working temperature is relatively high, above 200° C., increasing the economics costs of the composite material and mechanical or structured parts due to implication of high energy costs. Additionally thermoplastic polymers tend to degrade if the temperature is too high, which is especially true for semicrystalline thermoplastic polymers that have high melting points as for example polyamides such as PA6.6, polyethersulfon (PES), polyetherimid (PEI), polyetheretherketon (PEEK) or polyphenylene sulfide (PPS). This thermoinduced degradation yields to a decreasing molecular weight of the polymer matrix on the fibrous substrate important for the cohesion of the composite material and the mechanical or structured parts.

Another way for impregnating the fibrous substrate is to dissolve the thermoplastic polymer in an organic solvent. However this method requires a lot of solvent that has to be evaporated. There are environmental issues in using large quantities of solvent in term of energy and pollution.

Still another way is for impregnating the fibrous substrate is to use the respective monomers for the impregnation and polymerize to form the thermoplastic polymer after the impregnation. However this method usually uses monomers that might evaporate partly or have an unpleasant smell. There are also environmental issues in using certain monomers in an open environment.

These are the limits or disadvantages for the preparation of thermoplastic composite materials especially with fibrous reinforcements, the impregnation process for a fibrous substrate and the manufactured mechanical or structured parts or articles comprising said thermoplastic composite material.

The objective of the present invention is to solve the disadvantages mentioned above.

One objective of the present invention is to have a structural part comprising a thermoplastic composite material with satisfying mechanical properties such as high stiffness and a young modulus of at least 8 GPa.

Another objective of the present invention is to have a structural part comprising a thermoplastic composite material with a satisfying UV resistance.

The further objective of the present invention is to have a structural part comprising a thermoplastic composite material that can be transformed and shaped into form due to a certain flexibility.

A still further objective of the present invention is to have a piece or structural part comprising a thermoplastic composite material that is quit large, and the impregnation process for a fibrous substrate of large dimension.

Still another objective of the present invention is to wet completely, correctly and in a homogenous way the fibrous substrate during impregnation. Any defects of fiber wetting for example by bubbles and voids decrease the mechanical performance of the structural part.

Still another objective of the present invention is to propose a impregnation process for fibrous substrate and a liquid impregnation syrup with a lower or low volatile organic compound (VOC) content.

Still another objective of the present invention is to propose an impregnation process for fibrous substrate and a liquid impregnation syrup with lower flashpoint, less loss of raw materials due to evaporation.

Still another objective of the present invention is to have an impregnation process for a fibrous substrate that could contain a large quantity of additives and fillers.

Still another objective of the present invention is to manufacture a piece or structural part comprising a thermoplastic composite material that is has a better stability and less surface markings.

Another objective of the present invention is the recycling of the structural part including the composite material or structural parts that do not meet quality standards or worn-out structural parts. Under recycling is understood to recover at least a part of the used raw materials. This means grinding and reusing the thermoplastic polymer. This means also for example that the monomer from the thermoplastic matrix of the composite material can be recovered.

Another objective of the present invention is to provide a process to produce the structural parts comprising the thermoplastic composite material of the invention at a reaction at lower temperature (ambient) and generating less exothermal energy.

Another objective of the present invention is to provide a process which can be carried out at low cost and is capable of large-scale manufacturing, to produce the structural parts comprising the thermoplastic composite material of the invention. In addition, the process should be easy and simple to carry out using commercially available components. Also the manufacturing of parts should be reproducible and fast meaning short cycle times.

BACKGROUND OF THE INVENTION

Prior Art

The document FR1374046 describes a process of polymerization of acrylic monomers especially methacrylic monomers from monomer-polymer syrups using a metal catalyst based on tin. Glass fibres are impregnated with a methanol solution of the tin catalyst. Afterwards the fibres are impregnated with a monomer-polymer syrup and then the composition is polymerized. The process uses a metal catalyst and the impregnation is made with a liquid syrup based on methyl methacrylate.

The document JP9085841 describes the preparation of a fabric base composite thermoplastic plastic member. A thermoplastic polymer is dissolved in a volatile solvent and mixed with the fabric base material. The solvent is evaporated and the prepreg is cut into shapes, then it is coated again with the solution of thermoplastic polymer in a solvent and cured by evaporation of the solvent. In the example a polymethylmethacrylate as thermoplastic polymer is dissolved at 15 wt % in a solvent mixture consisting of methanol, xylene, tetrahydrofyran in order to impregnate the fibrous material. This preparation method uses a lot of solvent that evaporates.

The document EP0796873 discloses a (meth)acrylic syrup, a process for preparing the syrup and a process for preparing molding material containing the (meth)acrylic syrup. The main objective is having a syrup with excellent storage stability. The molding material might include a reinforcing material in form of fibres. The syrup comprises mainly methyl methacrylate and in lesser quantity a vinyl monomers.

The document WO2013/056845 discloses a thermoplastic composite material obtained by in situ polymerization of a thermoplastic resin with a fibrous material. More particularly the present invention relates to a polymeric composite material obtained by in-situ polymerization of a thermoplastic (meth) acrylic resin and a fibrous material containing long fibers and its use, a process for making such a composite material and manufactured mechanical or structured part or article comprising this polymeric composite material. The (meth)acrylic resin comprises mainly methyl methacrylate as main monomer that has a boiling point of about 101° C. at 1013 mbar and a vapor pressure of about 26.7 mbar at 20° C.

In the prior art there is either no impregnation process for impregnating a fibrous substrate as described where the fibrous substrate and the liquid monomeric syrup are brought into contact before the polymerization according to the present invention or impregnation process for impregnating a fibrous substrate uses mainly methyl methacrylate monomer as main component in the syrup or another monomer having a boiling point less than 115° C. at 1013 mbar and a vapor pressure above 25 mbar at 20° C.

In the prior art no manufacturing process for manufacturing mechanical or structured parts or articles is described including the impregnation process for impregnating a fibrous substrate with the composition of a liquid monomeric syrup and polymerization according to the present invention.

BRIEF DESCRIPTION OF THE INVENTION

Surprisingly it has been found that an impregnation process for impregnating a fibrous substrate, wherein said fibrous substrate is made of long fibres and said process comprises a step of impregnating said fibrous substrate with a liquid monomer syrup comprising:
  a) a (meth)acrylic polymer,
  b) at least one monomer (A) chosen from a (meth) acrylic monomer or a vinyl monomer or mixture therof, c) at least one initiator or initiating system for starting the polymerization of the monomer or monomers, d) optionally another (meth) acrylic monomer (B), wherein the at least one monomer (A) chosen from (meth) acrylic monomer or vinylic monomers has a boiling point of at least 115° C. at 1013 mbar and/or a vapour pressure of less than 25 mbar at 20° C. and wherein the other (meth)acrylic monomer (B) has a boiling point less than 115° C. at 1013 mbar and/or a vapour pressure of more than 25 mbar at 20° C., and wherein said liquid monomer syrup has a dynamic viscosity of a value in the range from 10 mPa*s to 10000 mPa*s, preferably from 50 mPa*s to 5000 mPa*s and advantageously from 100 mPa*s to 1000 mPa*s yields to a complete and correct impregnation of the fibrous substrate.

Surprisingly it has also been discovered that an impregnation liquid monomer syrup for implementing the impregnation process for a fibrous substrate, said liquid monomer syrup comprises:

a) a (meth)acrylic polymer, b) at least one monomer (A) chosen from a (meth) acrylic monomer or a vinyl monomer or mixture therof, c) at least one initiator or initiating system for starting the polymerization of the monomer or monomers, d) optionally another (meth) acrylic monomer (B), wherein the at least one monomer (A) chosen from (meth) acrylic monomer or vinylic monomers has a boiling point of at least 115° C. at 1013 mbar and/or a vapour pressure of less than 25 mbar at 20° C. and wherein the other (meth)acrylic monomer B has a boiling point less than 115° C. at 1013 mbar and/or a vapour pressure of more than 25 mbar at 20° C., and wherein said liquid monomer syrup has a dynamic viscosity of a value in the range from 10 mPa*s to 10000 mPa*s, preferably from 50 mPa*s to 5000 mPa*s and advantageously from 100 mPa*s to 1000 mPa*s yields to a complete and correct impregnation of the fibrous substrate.

Surprisingly it has also been discovered that a manufacturing process for manufacturing mechanical or structured parts or articles comprising following steps:

a) impregnating a fibrous substrate with a liquid monomer syrup, said liquid monomer syrup comprises:
  i) a (meth)acrylic polymer,
  ii) at least one monomer (A) chosen from a (meth) acrylic monomer or a vinyl monomer or mixture therof,
  iii) at least one initiator or initiating system for starting the polymerization of the monomer or monomers,
  iV) optionally another (meth) acrylic monomer (B),
  wherein the at least one monomer (A) chosen from (meth) acrylic monomer or vinylic monomers has a boiling point of at least 115° C. at 1013 mbar and/or a vapour pressure of less than 25 mbar at 20° C. and
  wherein the other (meth)acrylic monomer (B) has a boiling point less than 115° C. at 1013 mbar and/or a vapour pressure of more than 25 mbar at 20° C.,
  and wherein said liquid monomer syrup has a dynamic viscosity of a value in the range from 10 mPa*s to 10000 mPa*s, preferably from 50 mPa*s to 5000 mPa*s and advantageously from 100 mPa*s to 1000 mPa*s yields to a complete and correct impregnation of the fibrous substrate b) polymerising the liquid monomer syrup impregnating said fibrous substrate yields to manufactured mechanical or structured parts or articles having satisfying mechanical properties by possessing a high stiffness and a young modulus of at least 8 GPa.

Additionally it has also been discovered that a three-dimensional mechanical or structured parts obtained by the manufacturing process possessing a high stiffness and a young modulus of at least 8 GPa, has nearly no defects as voids between the fibrous substrate and the polymer.

DETAILED DESCRIPTION OF THE INVENTION

According to a first aspect, the present invention relates to an impregnation process for impregnating a fibrous substrate, wherein said fibrous substrate is made of long fibres and said process comprises a step of impregnating said fibrous substrate with a liquid monomer syrup comprising:

a) a (meth)acrylic polymer, b) at least one monomer (A) chosen from a (meth) acrylic monomer or a vinyl monomer or mixture therof, c) at least one initiator or initiating system for starting the polymerization of the monomer or monomers, d) optionally another (meth) acrylic monomer (B), wherein the at least one monomer (A) chosen from (meth) acrylic monomer or vinylic monomers has a boiling point of at least 115° C. at 1013 mbar and/or a vapour pressure of less than 25 mbar at 20° C. and wherein the other (meth)acrylic monomer B has a boiling point less than 115° C. at 1013 mbar and/or a vapour pressure of more than 25 mbar at 20° C., and wherein said liquid monomer syrup has a dynamic viscosity of a value in the range from 10 mPa*s to 10000 mPa*s, preferably from 50 mPa*s to 5000 mPa*s and advantageously from 100 mPa*s to 1000 mPa*s.

According to another aspect the impregnation process of the fibrous substrate of the present invention is made in a mold.

According to still another aspect the impregnation process of the fibrous substrate of the present invention is made with a liquid monomer syrup that comprises a (meth)acrylic polymer which is a homo- or copolymer of methyl methacrylate (MMA) or a mixture thereof.

By the term "fibrous substrate" as used are denoted fabrics, felts or nonwovens that may be in the form of strips, laps, braids, locks or pieces.

By the term "vinyl monomer" as used is denoted all kind of monomers that comprise a $H_2C=CHR$ structure.

By the term "(meth)acrylic" as used is denoted all kind of acrylic and methacrylic monomers.

By the term "PMMA" as used are denoted homo- and copolymers of methylmethacrylate (MMA), for the copolymer of MMA the weight ratio of MMA inside the PMMA is at least 70 wt %.

By the term "monomer" as used is denoted is a molecule which can under go polymerization.

By the term "polymerization" as used is denoted the process of converting a monomer or a mixture of monomers into a polymer.

By the term "thermoplastic polymer" as used is denoted a polymer that turns to a liquid or becomes more liquid or less viscous when heated and that can take on new shapes by the application of heat and pressure.

By the term "thermosetting polymer" as used is denoted a prepolymer in a soft, solid or viscous state that changes irreversibly into an infusible, insoluble polymer network by curing.

By the term "polymer composite" as used is denoted a multicomponent material comprising multiple different phase domains in which at least one type of phase domain is a continuous phase and in which at least one component is a polymer.

By the term "initiator" as used is denoted a chemical species that's reacts with a monomer to form an intermediate compound capable of linking successively with a large number of other monomers into a polymeric compound.

By the term "boiling point" of a substance as used is denoted the temperature at which the vapor pressure of the liquid equals the pressure surrounding the liquid and the liquid changes into a vapor.

By the term "vapour pressure" of a substance as used is denoted the pressure exerted by a vapor in thermodynamic equilibrium with its condensed phases (solid or liquid) at a given temperature.

With regard to structured part or article this concerns a panel, a cover or a hull made of composite material or parts for aircrafts, for boats (hull and deck), rail cars (hatch, partition, body), and automotive parts (car body, hood, door.)

With regard to the (metha)acrylic polymer, one could mention poly alkyl methacrylates or poly alkyl acrylates. In a preferred embodiment the (meth)acrylic polymer is poly methyl methacrylate (PMMA).

The term "PMMA" denotes a methyl methacrylate (MMA) homopolymer or a copolymer or mixtures thereof.

In one embodiment the homo- or copolymer of methyl methacrylate (MMA) comprises at least 70%, preferably at least 80%, advantageously at least 90% and more advantageously at least 95% by weight of methyl methacrylate.

In another embodiment the PMMA is a mixture of at least one homopolymer and at least one copolymer of MMA, or a mixture of at least two homopolymers or two copolymers of MMA with a different average molecular weight or a mixture of at least two copolymers of MMA with a different monomer composition.

The copolymer of methyl methacrylate (MMA) comprises from 70% to 99.7% by weight of methyl methacrylate and from 0.3 to 30% by weight of at least one monomer having at least one ethylenic unsaturation that can copolymerize with methyl methacrylate.

These monomers are well known and mention may be made, in particular of acrylic and methacrylic acids and alkyl-(meth)acrylates in which the alkyl group has from 1 to 12 carbon atoms. As examples, mention may be made of methyl acrylate and ethyl, butyl or 2-ethylhexyl (meth) acrylate. Preferably the comonomer is an alkyl acrylate in which the alkyl group has from 1 to 4 carbon atoms.

In a preferred embodiment the copolymer of methyl methacrylate (MMA) comprises from 70% to 99.7%, preferably from 80% to 99.7% advantageously from 90% to 99.7% and more advantageously from 90% to 99.5% by weight of methyl methacrylate and from 0.3% to 30%, preferably from 0.3% to 20% advantageously from 0.3% to 10% and more advantageously from 0.5% to 10% by weight of at least one monomer having at least one ethylenic unsaturation that can copolymerize with methyl methacrylate. Preferably the comonomer is chosen from methyl acrylate or ethyl acrylate or mixtures thereof.

The weight average molecular weight of the (meth)acrylic polymer should be high, meaning larger than 50 000 g/mol, preferably larger than 100 000 g/mol.

The weight average molecular weight can be measured by size exclusion chromatography (SEC).

With regard to the monomer (A) of the syrup according to the invention, it chosen from a (meth) acrylic monomer or a vinyl monomer or mixture therof.

The monomer (A) has a boiling point of at least 115° C. at 1013 mbar and/or a vapour pressure of less than 25 mbar at 20° C.

Preferably the monomer (A) has vapour pressure of less than 10 mbar at 20° C.

Preferably the monomer (A) has boiling point of at least 135° C. at 1013 mbar.

Advantageously the monomer (A) is chosen from cyclohexyl methacrylate, isobornyl acrylate, isobornyl methacrylate, heptyl methacrylate, n-octyl acrylate, 2-octyl acrylate, iso-octyl acrylate, 2-ethylhexyl methacrylate, butyl diglycol methacrylate, dicyclopentenyloxyethyl methacrylate, ethoxy ethyl methacrylate, isobutyl methacrylate, n-butyl methacrylate, tert-butyl methacrylate, hydroxyl propyl methacrylate, styrene, alpha methyl styrene, ortho-, beta- or para-methyl styrene, tert-butyl styrene, nitro styrene, N-vinylpyrrolidone and mixtures therof.

More advantageously the monomer (A) is chosen from cyclohexyl methacrylate, isobornyl acrylate, isobornyl methacrylate, heptyl methacrylate, dicyclopentenyloxyethyl methacrylate, ethoxy ethyl methacrylate, isobutyl methacrylate, n-butyl methacrylate, tert-butyl methacrylate, hydroxyl propyl methacrylate and mixtures therof.

Even more advantageously the monomer (A) is chosen from cyclohexyl methacrylate, isobornyl methacrylate, heptyl methacrylate, dicyclopentenyloxyethyl methacrylate, ethoxy ethyl methacrylate, isobutyl methacrylate, n-butyl methacrylate, tert-butyl methacrylate, hydroxyl propyl methacrylate and mixtures therof.

In a most advantageously embodiment the monomer (A) is chosen from cyclohexyl methacrylate.

With regard to the optional (meth)acrylic monomer (B), it is chosen from alkyl acrylic monomers, alkyl methacrylic monomers and mixtures thereof.

The monomer (B) has a boiling point less than 115° C. at 1013 mbar and/or a vapour pressure of at least 25 mbar at 20° C.

Preferably the monomer (B) is chosen from alkyl acrylic monomers the alkyl group having from 1 to 4 carbons, either linear or branched or methyl methacrylate and mixtures thereof.

Advantageously the (meth)acrylic monomer is chosen from methyl methacrylate, methyl acrylate, ethyl acrylate and mixtures thereof.

In a preferred embodiment at least 50 wt %, preferably at least 60 wt % of the monomer (B) is methyl methacrylate.

In a more preferred embodiment at least 50 wt %, preferably at least 60 wt %, more preferably at least 70 wt % and advantageously at least 80 wt % and even more advantageously 90 wt % of the monomer (B) is a mixture of methyl methacrylate with ethyl methacrylate, methyl acrylate, ethyl acrylate, iso-butyl acrylate or.

With regard to the fibrous substrate, one can mention fabrics, felts or nonwovens that may be in the form of strips, laps, braids, locks or pieces. The fibrous material can have different forms and dimensions either one dimensional, two dimensional or three dimensional. A fibrous substrate comprises an assembly of one or more fibres. When the fibres are continuous, their assembly forms fabrics.

The one dimensional form is linear long fibres. The fibers may be discontinuous or continuous. The fibers may be arranged randomly or as a continuous filament parallel to each other. A fiber is defined by its aspect ratio, which is the ratio between length and diameter of the fiber. The fibers used in the present invention are long fibers or continuous fibers. The fibers have an aspect ratio of at least 1000, preferably at least 1500, more preferably at least 2000, advantageously at least 3000, more advantageously at least 5000, even more advantageously at least 6000 most advantageously at least 7500 and at most advantageously at least 10 000.

The two dimensional form are fibrous mats or non woven reinforcements or woven roving or bundles of fibers, which can also be braded. Even if these two dimensional forms have a certain thickness and therefore in principle a third dimension, they are considered as two dimensional according to the present invention.

The three dimensional form are for example stacked or folded fibrous mats or non woven reinforcements or bundles of fibers or mixtures thereof, an assembly of the two dimensional form in the third dimension.

The origins of the fibrous material can be a natural or a synthetic one. As natural material one can mention vegetable fibers, wood fibers, animal fibers or mineral fibers.

Natural fibers are for example sisal, jute, hemp, flax, cotton, coconut fibers, and banana fibers. Animal fibers are for example wool or hair.

As synthetic material one can mention polymeric fibers chosen from fibers of thermosetting polymers, from thermoplastic polymers or their mixtures.

The polymeric fibers can be made of polyamide (aliphatic or aromatic), polyester, polyvinylacohol, polyolefins, polyurethanes, polyvinylchloride, polyethylene, unsatured polysters, epoxy resins and vinylesters.

The mineral fibers can also be chosen from glass fibers especially of type E, R or S2, carbon fibers, boron fibers or silica fibers.

The fibrous substrate of the present invention is chosen from vegetable fibers, wood fibers, animal fibers, mineral fibers, synthetic polymeric fibers, glass fibers, carbon fibers or mixtures thereof.

Preferably the fibrous substrate is chosen from mineral fibers.

The fibres of the fibrous material have a diameter between 0.005 µm and 100 µm, preferably between 1 µm and 50 µm, more preferably between 5 µm and 30 µm and advantageously between 10 µm and 25 µm.

Preferably the fibres of the fibrous material of the present invention are chosen from continuous fibres (meaning that the aspect ratio does not apply as for long fibres) for the one dimensional form, or long or continuous fibres forming the two or three dimensional form of the fibrous substrate.

With regard to the initiator or initiating system for starting the polymerization of the monomer (A) and the optional (meth) acrylic monomer (B), one could mention initiators or initiating systems that are activated by heat.

The heat activated initiator is preferably a radical initiator.

With regard to the radical initiator, they can be chosen from diacyl peroxides, peroxy esters, dialkyl peroxides, peroxyacetals, hydro peroxides or azo compounds.

The initiator or initiating system for starting the polymerization of the (meth) acrylic monomer is chosen from isopropyl carbonate, benzoyl peroxide, lauroyl peroxide, caproyl peroxide, dicumyl peroxide, tert-butyl perbenzoate, tert-butyl per(2-ethylhexanoate), cumyl hydroperoxide, 1,1-di(tert-butylperoxy)-3,3,5-trimethylcyclohexane, tert-butyl peroxyisobutyrate, tert-butyl peracetate, tert-butyl perpivalate, amyl perpivalate, tert-butyl peroctoate, azobisisobutyronitrile (AIBN), azobisisobutyramide, 2,2'-azobis(2,4-dimethylvaleronitrile) or 4,4'-azobis(4-cyanopentanoic). It would not be departing from the scope of the invention to use a mixture of radical initiators chosen from the above list.

Preferably the initiator or initiating system for starting the polymerization of the monomer (A) and the optional (meth) acrylic monomer (B) is chosen from peroxides having 2 to 20 carbon atoms.

The content of radical initiator with respect to the monomer (A) and the optional (meth) acrylic monomer (B) of the liquid monomer syrup is from 100 to 50000 ppm by weight (50000 ppm=5 wt %), preferably between 200 and 40000 ppm by weight and advantageously between 300 and 30000 ppm.

The monomer (A) and the optional (meth) acrylic monomer (B) is/are typically one or more monomers as defined above with, optionally, a suitable inhibitor such as hydroquinone (HQ), methyl hydroquinone (MEHQ), 2,6-di-tertiary-butyl-4-methoxyphenol (Topanol O) and 2,4-dimethyl-6-tertiary-butyl phenol (Topanol A).

The inhibitor is present to prevent the monomer from spontaneously polymerising.

The liquid monomer syrup comprises optionally also an activator for the polymerization. Polymerisation activator or accelerator is chosen from tertiary amines such as N,N-dimethyl-p-toluidine (DMPT), N,N-dihydroxyethyl-p-toluidine (DHEPT), organic-soluble transition metal catalysts or mixtures thereof.

Advantageously the liquid monomer syrup contains no activators for catalytically accelerate the polymerization reaction as cobalt or tin based compounds and especially tin chloride.

The content of the activator with respect to the to the monomer (A) and the optional (meth) acrylic monomer (B) of the liquid monomer syrup is from 100 ppm to 20000 ppm (by weight), preferably from 200 ppm to 10000 ppm by weight and advantageously from 300 ppm to 7000 ppm.

The presence of activators or accelerators depends upon the final application. Where "cold-cure" is necessary or wished, an accelerator is usually necessary. Cold cure means that the polymerization takes place at ambient temperature, meaning less than 50° C. or preferably less than 40° C.

However, for industrial applications the use of heat in "heat-cure" systems is also possible.

Another ingredient in the liquid resin can also be a chain-limiting agent in order to control the molecular weight, for example γ-terpinene or terpinolene, at contents of between 0 and 500 ppm and preferably between 0 and 100 ppm, with respect to the monomers of the mixture.

The impregnation process according to the invention for impregnating a fibrous substrate comprises a step of impregnating the fibrous substrate with a liquid monomer syrup.

A simple monomer (A) and the optional (meth) acrylic monomer (B) or a monomer mixture as liquid monomer syrup is too liquid for the impregnation process of the present invention, especially for the correct and complete wetting and impregnation of the fibrous substrate. Therefore the viscosity has to be adapted by increasing it.

With regard to the liquid monomer syrup according to the invention that impregnates the fibrous substrate, it comprises a monomer (A.), optionally a (meth)acrylic monomer (B) or a mixture of a (meth)acrylic monomers (B), a (meth)acrylic polymer and at least one initiator or initiating system for starting the polymerization of the respective monomer or monomers.

According to the invention the viscosity is increased by using monomer (A) or a mixture of monomers (A) and optionally a (meth)acrylic monomer (B) with dissolved (meth)acrylic polymer or (meth)acrylic polymers. This solution is commonly referred to as "syrup" or "prepolymer".

Advantageously the liquid monomer syrup contains no additionally voluntary added solvent.

The (meth)acrylic polymer is completely soluble in the monomer (A) or mixture of monomers (A) and (B).

This (meth)acrylic polymer is PMMA, meaning the homo- or copolymer of methyl methacrylate (MMA) or a mixture thereof as defined before.

This monomer (A) and (meth)acrylic monomer (B) are the same as defined before.

The monomer (A) presents more than 30 wt %, preferably more than 35 wt %, more preferably more than 40 wt %, advantageously more than 45 wt % and more advantageously more than 50 wt % of the total sum of monomers (A) and (B) present in the liquid monomer syrup.

The (meth)acrylic monomer (B) presents less than 70 wt %, preferably less than 65 wt %, more preferably less than 60 wt %, advantageously less than 55 wt %, and more advantageously less than 50 wt % of the total sum of monomers (A) and (B) in the liquid monomer syrup.

The monomer (A) or the sum of monomer (A) and (meth)acrylic monomer (B) in the liquid monomer syrup present at least 30% by weight, preferably 40% by weight, advantageously 50% by weight and more advantageously 60% by weight of total weight of compounds a)+b)+c)+d) of the liquid monomer syrup.

The monomer (A) or the sum of monomer (A) and (meth)acrylic monomer (B) in the liquid monomer syrup present at most 95% by weight, preferably at most 90% by weight, advantageously at most 85% by weight and more advantageously at most 80% by weight of total weight of compounds a)+b)+c)+d) of the liquid monomer syrup.

The (meth)acrylic polymer or polymers in the liquid monomer syrup present at least 5% by weight, preferable at least 10%, advantageously at least 15% and more advantageously at least 20% by weight of total weight of compounds a)+b)+c)+d) of the liquid monomer syrup.

The (meth)acrylic polymer or polymers in the liquid monomer syrup present at most 60% by weight, preferable at most 50%, advantageously at most 40% and more advantageously at most 35% by weight of total weight of compounds a)+b)+c)+d) of the liquid monomer syrup.

The monomer (A) or the sum of monomer (A) and (meth)acrylic monomer (B) in the liquid monomer syrup presents from 30% to 90% by weight, preferably from 40% to 90% by weight, advantageously from 50% to 85% by weight and more advantageously from 60% to 80% by weight of total weight of compounds a)+b)+c)+d) of the liquid monomer syrup.

Accordingly (meth)acrylic polymer or polymers in the liquid monomer syrup presents from 60% to 5% by weight, preferably from 60% to 10% by weight, advantageously from 15% to 50% by weight and more advantageously from 20% to 40% by weight of total weight of compounds a)+b)+c)+d) of the liquid monomer syrup.

The dynamic viscosity of the liquid monomer syrup is in a range from 10 mPa*s to 10000 mPa*s, preferably from 50 mPa*s to 5000 mPa*s and advantageously from 100 mPa*s to 1000 mPa*s and more advantageously 100 mPa*s to 500 mPa*s. The viscosity of the syrup can be easily measured with a Rheometer or viscosimeter. The dynamic viscosity is measured at 25° C. The liquid monomer syrup has a Newtonian behaviour, meaning no shear thinning, so that the dynamic viscosity is independent of the shearing in a rheometer or the speed of the mobile in a viscosimeter.

If the viscosity of the liquid monomer syrup at a given temperature is too high for the impregnation process and for the correct impregnation, it is possible to heat the syrup in order to have a more liquid syrup within the before mentioned dynamic viscosity interval at the respective temperature during which the impregnation takes place for the sufficient wetting and correct and complete impregnation of the fibrous substrate.

The liquid syrup according to the present invention does not contain any additional solvent voluntary added.

The liquid monomer syrup may comprise also other additives and fillers. A filler in the scope of the present invention is not considered as an additive.

All the additives and fillers can be added to the liquid monomer syrup before the impregnation.

As additives one can mention organic additives as impact modifiers or block copolymers, thermal stabilizers, UV stabilizers, lubricants, dispersants, antifoaming agents, rheology modifiers, waxes, adhesion modifiers, mold release agents and mixtures thereof.

The impact modifier is in the form of fine particles having an elastomeric core and at least one thermoplastic shell, the size of the particles being in general less than 1 μm and advantageously between 50 and 300 nm. The impact modifier is prepared by emulsion polymerization. The impact modifier content in the liquid monomer syrup is from 0 to 50 wt %, preferably from 0 to 25 wt %, and advantageously from 0 to 20% by weight.

As fillers one can mention carbon nanotubes or mineral charges including mineral nano charges (TiO2, silica) and carbonates and hydrates.

The filler content in the liquid monomer syrup is from 0 wt % to 60 wt %.

An additional aspect according to the present invention is the impregnation process, for impregnating a fibrous substrate, wherein said fibrous substrate is made of long fibres and said process comprises a step of impregnating said fibrous substrate with a liquid (meth) acrylic syrup comprising:
  a) from 5 wt % to 59.99 wt % (meth)acrylic polymer,
  b) from 30 wt % to 89.99 wt % sum of monomer (A) and optionally monomer (B),
  c) from 0.01 wt % to 5 wt % one initiator or initiating system for starting the polymerization of the (meth) acrylic monomer,
  d) from 0 wt % to 1 wt % activator,
  e) from 0 wt % to 60 wt % filler,
  f) from 0 wt to 20 wt % additives.
wherein the at least one monomer (A) chosen from (meth)acrylic monomer or vinylic monomers has a boiling point of at least 115° C. at 1013 mbar and/or a vapour pressure of less than 25 mbar at 20° C. and
wherein the other (meth)acrylic monomer B has a boiling point less than 115° C. at 1013 mbar and/or a vapour pressure of more than 25 mbar at 20° C.
said liquid (meth)acrylic syrup has a dynamic viscosity of a value in the range from 10 mPa*s to 10000 mPa*s, preferably from 50 mPa*s to 5000 mPa*s and advantageously from 100 mPa*s to 1000 mPa*s.

The respective compounds are the same as defined before.

Another additional aspect according to the present invention is the impregnation liquid (meth) acrylic syrup for implementing the impregnation process according to any of the preceding claims, said liquid (meth) acrylic syrup comprises a) a (meth)acrylic polymer,
b) at least one monomer (A) chosen from a (meth) acrylic monomer or a vinyl monomer or mixture therof,
c) at least one initiator or initiating system for starting the polymerization of the (meth) acrylic monomer,
d) optionally another (meth) acrylic monomer (B)

wherein the at least one monomer (A) chosen from (meth) acrylic monomer or vinylic monomers has a boiling point of at least 115° C. at 1013 mbar and/or a vapour pressure of less than 25 mbar at 20° C. and
wherein the other (meth)acrylic monomer B has a boiling point less than 115° C. at 1013 mbar and/or a vapour pressure of more than 25 mbar at 20° C.
said liquid (meth)acrylic syrup has a dynamic viscosity of a value in the range from 10 mPa*s to 10000 mPa*s, preferably from 50 mPa*s to 5000 mPa*s and advantageously from 100 mPa*s to 1000 mPa*s.
The respective compounds are the same as defined before.

Still another additional aspect according to the present invention is an impregnation liquid (meth) acrylic syrup comprising:
  from 5 wt % to 59.99 wt % (meth)acrylic polymer, from 30 wt % to 89.99 wt % sum of monomer (A) and optinally monomer (B),
  from 0.01 wt % to 5 wt % one initiator or initiating system for starting the polymerization of the (meth) acrylic monomer,
  from 0 wt % to 1 wt % activator,
  from 0 wt % to 60 wt % fillers,
  from 0 wt to 20 wt % additives.

Still another aspect of the present invention is a manufacturing process for manufacturing mechanical or structured parts or articles comprising following steps:
  a) impregnating a fibrous substrate with a liquid monomer syrup,
  b) polymerising the liquid monomer syrup impregnating said fibrous substrate.

The respective compounds are the same as defined before.

Preferably the impregnation of the fibrous substrate in step a) is made in a mold.

Advantageously the step a) and step b) are made in the same mould.

The mold is opaque towards visible and ultraviolet radiation at least on one side Using the same mold will avoid the transfer of the material after impregnation.

The temperature of the polymerization is step b) is below 120° C., preferably below 80° C. and more preferably below 40° C. By polymerization temperature is meant the temperature where the polymerization starts. No external heating beyond this temperature is required (for example of the mold) in order to start the polymerization. During the polymerization the temperature inside can achieve peaks that go beyond this temperature of polymerization.

No tin is present in manufactured mechanical or structured parts or articles coming from accelerators added for the polymerization step.

The manufactured mechanical or structured parts or articles do not contain any additional solvent voluntary added, since the syrup did not contain any additional solvent for the impregnation step.

With regard to the manufactured mechanical or structured parts or articles of the present invention, it comprises at least 20% by weight of fibrous substrate, preferable at least 40% by weight of fibrous material advantageously at least 50% by weight of fibrous material and advantageously at least 55% by weight of fibrous material based on the total composition.

The manufactured mechanical or structured parts or articles of the present invention, it comprises at most 99% by weight of fibrous material, preferable at most 95% by weight of fibrous material advantageously at most 90% by weight of fibrous material and advantageously at most 80% by weight of fibrous material based on the total composition.

Due to the manufacturing process for manufacturing mechanical or structured parts or articles according to the invention a complete, correct and homogenous wetting of the fibrous substrate during impregnation takes place. There are no defects of fiber wetting during impregnation for example by bubbles and voids that decrease the mechanical performance of the manufacturing mechanical or structured parts or articles.

The manufactured mechanical or structured parts or articles according to the invention do not comprise essentially any pores. By pore is meant a spherical void with a diameter of at least 1 μm or larger or an elongated ellipsoidal void in form of an oblate with a smallest principal axe of at least 0.5 μm or larger. By "comprising essentially no pores" is meant that the pores represent less then 1 vol %, preferably less then 0.5 vol % and more preferably less then 0.2 vol % of the total volume of the manufactured mechanical or structured parts or articles.

With regard to manufacturing process for manufacturing mechanical or structured parts or articles comprising the polymeric composite material, several methods could be used in order to prepare three-dimensional mechanical or structured parts. One can mention infusion, vacuum bag moulding, pressure bag molding, autoclave molding, resin transfer moulding (RTM), reaction injection molding (RIM) reinforced reaction injection molding (R-RIM) and variants thereof, press molding, compression molding or pultrusion, hand lay up, spray-up, filament widing, sheet molding compound process or bulk molding compound process.

The preferred manufacturing process for manufacturing mechanical or structured parts or articles comprising the composite materials are processes were the liquid monomer syrup transferred to the fibrous substrate by impregnating the fibrous substrate in a mold.

Advantageously the impregnation step of the fibrous material is made in a mold.

Most advantageously the manufacturing process for manufacturing mechanical or structured parts or articles comprising the polymeric composite material is chosen from pultrusion, hand lay up, spray-up, resin transfer molding or infusion.

All processes comprise the step of impregnating the fibrous substrate with the liquid monomer syrup before the polymerization step in a mold.

The step of polymerising of the liquid monomer syrup impregnating said fibrous substrate takes place after the impregnation step in the same mold.

In the pultrusion method a long continuous product of constant cross section is produced. The fibers coming from creels are wetted and impregnated with the liquid resin in a resin bath followed by preforming, shaping and polymerization.

Resin transfer molding is a method using a two sided mold set which forms both surfaces of composite material. The lower side is a rigid mould. The upper side can be a rigid or flexible mould. Flexible moulds can be made from composite materials, silicone or extruded polymer films such as nylon. The two sides fit together to produce a mould cavity. The distinguishing feature of resin transfer moulding is that the fibrous substrate is placed into this cavity and the mould set is closed prior to the introduction of the liquid monomer syrup. Resin transfer moulding includes numerous varieties which differ in the mechanics of how the liquid (meth) acrylic syrup is introduced to the fibrous substrate in the mould cavity. These variations include everything from vacuum infusion to vacuum assisted resin transfer moulding (VARTM). This process can be performed at either ambient or elevated temperature. Ambient temperature means between 10° C. and 50° C. Elevated temperature means up to 200° C. Preferably elevated temperature is from 50° C. up to 160° C.

With the infusion method the liquid monomer syrup does have to have the adapted viscosity towards this preparation method of the polymeric composite material. The liquid monomer syrup is aspired into the fibrous substrate present in a special mold by application of a slight vacuum. The fibrous substrate is infused and completely impregnated by the liquid monomer syrup.

One advantage of this method is the high amount of fibrous material in the composite.

With regard to the use of manufactured mechanical or structured parts or articles, one can mention automotive applications, nautical applications, railroad applications, sport, aeronautic and aerospace applications, photovoltaic applications, computer related applications, telecommunication applications and wind energy applications.

Particularly the three-dimensional mechanical or structured part is a automobile part, boat part, train part, sport article, plane or helicopter part, space ship or rocket part, photovoltaic module part, wind turbine part, furniture part, construction or building part, telephone or cell phone part, computer or television part, printer and photocopy part.

The impregnation process for impregnating a fibrous substrate or the manufacturing process for manufacturing mechanical or structured parts or articles is used for the manufacturing of recyclable mechanical and/or structural parts, which are recyclable by thermal depolymerisation, preferably with at least 50% of the monomers recovered.

EXAMPLES

Several mixtures are prepared by adding to a methacrylic monomer (M1) 2.5 parts per hundred by weight of benzoyl peroxide (BPO) and 0.3 parts per hundred by weight of DMPT (N,N-dimethyl-p-toluidine from Sigma-Aldrich). The respective methacrylic monomers M1 are methyl methacrylate, cyclohexyl methacrylate and tertbutyl methacrylate.

The mixture is polymerized in a recipient of 100 ml of volume at a surrounding temperature or 25±1° C. The temperature is measured with aid of a temperature detector put inside the mixture. The temperature increases as the polymerization progresses. After a certain time the temperature arrives at a peak and decreases again. The time at which the temperature peak occurs is compared in table 1 of the mixtures with the respective methacrylic monomers.

TABLE 1

| Methacrylic monomer M1 | Peak time/ [min] |
|---|---|
| methyl methacrylate | 75 |
| cyclohexyl methacrylate | 24 |
| tertbutyl methacrylate | 125 |

Example 1

A syrup is prepared by dissolving 20 parts by weight of the PMMA (BS520 a copolymer of MMA comprising ethyl acrylate as a comonomer) in 40 parts by weight of methyl methacrylate, which is stabilized with MEHQ (hydroquinone monomethyl ether) and 40 parts by weight of cyclohexyl methacrylate. To the 100 parts by weight of the syrup are added 2.5 parts by weight of benzoyl peroxide (BPO) and 0.3 parts by weight of DMPT (N,N-dimethyl-p-toluidine from Sigma-Aldrich). The syrup has a dynamic viscosity of 105 mPa*s at 25° C.

The syrup is polymerized in a recipient of 100 ml of volume at a surrounding temperature or 25±1° C. The temperature is measured with aid of a temperature detector put inside the syrup. After 20 minutes the temperature arrives at a peak.

Example 2

A syrup is prepared by dissolving 20 parts by weight of the PMMA (BS520 a copolymer of MMA comprising ethyl acrylate as a comonomer) in 34.5 parts by weight of methyl methacrylate, which is stabilized with MEHQ (hydroquinone monomethyl ether) and 45.5 parts by weight of cyclohexyl methacrylate. To the 100 parts by weight of the syrup are added 2.5 parts by weight of benzoyl peroxide (BPO) and 0.3 parts by weight of DMPT (N,N-dimethyl-p-toluidine from Sigma-Aldrich). The syrup has a dynamic viscosity of 103 mPa*s at 25° C.

The syrup is polymerized in a recipient of 100 ml of volume at a surrounding temperature or 25±1° C. The temperature is measured with aid of a temperature detector put inside the syrup. After 21 minutes the temperature arrives at a peak.

Comparative Example 1

A syrup is prepared by dissolving 20 parts by weight of the PMMA (BS520 a copolymer of MMA comprising ethyl acrylate as a comonomer) in 80 parts by weight of methyl methacrylate, which is stabilized with MEHQ (hydroquinone monomethyl ether). To the 100 parts by weight of the syrup are added 1.5 parts by weight of benzoyl peroxide (BPO) and 0.4 parts by weight of DMPT (N,N-dimethyl-p-toluidine from Sigma-Aldrich). The syrup has a dynamic viscosity of 120 mPa*s at 25° C.

The syrup is polymerized in a recipient of 100 ml of volume at a surrounding temperature or 25±1° C. The temperature is measured with aid of a temperature detector put inside the syrup. After 27 minutes the temperature arrives at a peak The odor of the syrups from example 1 and 2 is less intensive than the one from comparative example 1; concerning especially the characteristic odor of methyl methacrylate. Reactivity of polymerization is comparable or even better in view of kinetics as estimated by the peak of the exothermal energy generated by the polymerization that starts at ambient temperature (25° C.).

The invention claimed is:

1. An impregnation process for impregnating a fibrous substrate, wherein said fibrous substrate is made of long fibres having an aspect ratio of at least 1000, said fibers having a diameter between 0.005 micrometers and 100 micrometers, and said process comprises a step of impregnating said fibrous substrate with a liquid monomer syrup comprising:

a) a (meth)acrylic polymer,
b) at least one monomer (A) chosen from a (meth) acrylic monomer or a vinyl monomer or mixture thereof,
c) at least one initiator or initiating system for starting the polymerization of the (meth) acrylic monomer,
d) optionally another (meth) acrylic monomer (B)

wherein the at least one monomer (A) chosen from (meth) acrylic monomer or vinylic monomers has a boiling point of at least 115° C. at 1013 mbar and/or a vapour pressure of less than 25 mbar at 20° C. and
wherein the other (meth)acrylic monomer B has a boiling point less than 115° C. at 1013 mbar and/or a vapour pressure of more than 25 mbar at 20° C.,
and wherein said liquid monomer syrup has a dynamic viscosity of a value in the range from 10 mPa*s to 10000 mPa*s,
wherein monomer (A) is present at more than 50 wt % and (meth)acrylic monomer (B) presents less than 50 wt % of the total sum of monomers (A) and (B) present in the liquid monomer syrup, and wherein monomer (A) is selected from the group consisting of cyclohexyl methacrylate, isobornyl acrylate, isobornyl methacrylate, heptyl methacrylate, n-octyl acrylate, 2-octyl acrylate, iso-octyl acrylate, 2-ethylhexyl methacrylate, butyl diglycol methacrylate, dicyclopentenyloxyethyl methacrylate, ethoxy ethyl methacrylate, isobutyl methacrylate, n-butyl methacrylate, tert-butyl methacrylate, hydroxyl propyl methacrylate, styrene, alpha methyl styrene, ortho-, beta- or para-methyl styrene, tert-butyl styrene, nitro styrene, N-vinylpyrrolidone, and mixtures thereof.

2. The impregnation process according to claim 1, wherein monomer (A) has vapour pressure of less than 10 mbar at 20° C.

3. The impregnation process according to claim 1, wherein monomer (A) has boiling point of at least 135° C. at 1013 mbar.

4. The impregnation process according to claim 1, wherein the monomer syrup comprises the (meth) acrylic monomer (B).

5. The impregnation process according to claim 4, wherein the (meth)acrylic monomer (B) is chosen from alkyl acrylic monomers the alkyl group having from 1 to 4 carbons either linear or branched, methyl methacrylate and mixtures thereof.

6. The impregnation process according to claim 4, wherein the (meth)acrylic monomer (B) is chosen from methyl methacrylate, methyl acrylate, ethyl acrylate and mixtures thereof.

7. The impregnation process according to claim 1, wherein the (meth)acrylic polymer is a homo- or copolymer of methyl methacrylate (MMA) or a mixture thereof.

8. The impregnation process according to claim 7, wherein the copolymer of methyl methacrylate (MMA) comprises at least 70% by weight of methyl methacrylate (MMA).

9. The impregnation process according to claim 1, wherein the copolymer of methyl methacrylate (MMA) comprises from 70% to 99.7% by weight of methyl methacrylate and from 0.3 to 30% by weight of at least one monomer having at least one ethylenic unsaturation that can copolymerize with methyl methacrylate.

10. The impregnation process according to claim 9, wherein the comonomer is chosen from methyl acrylate or ethyl acrylate and a mixture thereof.

11. The impregnation process according to claim 1, wherein said initiator or initiating system for starting the polymerization of monomer (A) and the (meth) acrylic monomer (B) is generating radicals.

12. The impregnation process according to claim 1, wherein said initiator or initiating system for starting the polymerization of monomer (A) and the (meth) acrylic monomer (B) is chosen from diacyl peroxides, peroxy esters, dialkyl peroxides, peroxyacetals, hydroperoxides, azo compounds and mixtures thereof.

13. The impregnation process according to claim 1, wherein the (meth)acrylic polymer in the liquid monomer syrup present at least 5% by weight of total weight of compounds a)+b)+c)+d) of the liquid monomer syrup.

14. The impregnation process according to claim 1, wherein the (meth)acrylic polymer in the liquid (meth) acrylic syrup present at most 60% by weight of total weight of compounds a)+b)+c)+d) of the liquid monomer syrup.

15. The impregnation process according to claim 1, wherein the monomer (A) and the monomer (B) in the liquid monomer syrup present at least 30% by weight of total weight of compounds a)+b)+c)+d) of the liquid monomer syrup.

16. The impregnation process according to claim 1, wherein the liquid monomer syrup comprises:
a) from 5 wt % to 59.99 wt % (meth)acrylic polymer,
b) from 30 wt % to 89.99 wt % sum of monomer (A) and monomer (B),
c) from 0.01 wt % to 5 wt % one initiator or initiating system for starting the polymerization of the monomer or monomers,
d) from 0 wt % to 1 wt % activator,
e) from 0 wt % to 60 wt % filler, and
f) from 0 wt to 20 wt % additives.

17. A manufacturing process for manufacturing mechanical or structured parts or articles comprising following steps:
a) impregnating a fibrous substrate with a liquid monomer syrup according to claim 1, and
b) polymerising the liquid monomer syrup impregnating said fibrous substrate.

18. The process according to claim 17, wherein the impregnation of the fibrous substrate in step a) is made in a mold.

19. The process according to claim 17, wherein in step a) and step b) are made in the same mold.

20. The process according to claim 17, wherein the process is chosen from pultrusion, hand lay up, spray-up, resin transfer molding and infusion.

21. The process according to claim 17 wherein the temperature of the polymerization is step b) is below 120° C.

* * * * *